United States Patent
Berentsveig et al.

(10) Patent No.: US 10,206,404 B2
(45) Date of Patent: *Feb. 19, 2019

(54) DISINFECTANT

(71) Applicant: Saban Ventures Pty Limited, Lane Cove (AU)

(72) Inventors: Vladimir Berentsveig, Alexandria (AU); Dipika Patel, Alexandria (AU)

(73) Assignee: Saban Ventures Pty Limited, Lane Cove, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/651,601

(22) PCT Filed: Dec. 13, 2013

(86) PCT No.: PCT/AU2013/001463
§ 371 (c)(1),
(2) Date: Jun. 11, 2015

(87) PCT Pub. No.: WO2014/089633
PCT Pub. Date: Jun. 19, 2014

(65) Prior Publication Data
US 2015/0327554 A1 Nov. 19, 2015

(30) Foreign Application Priority Data

Dec. 14, 2012 (AU) .................. 2012905481

(51) Int. Cl.
*A01N 59/00* (2006.01)
*A61L 2/18* (2006.01)
*A01N 37/16* (2006.01)
*A01N 25/22* (2006.01)
*A01N 59/04* (2006.01)

(52) U.S. Cl.
CPC ............. *A01N 59/00* (2013.01); *A01N 25/22* (2013.01); *A01N 37/16* (2013.01); *A01N 59/04* (2013.01); *A61L 2/186* (2013.01)

(58) Field of Classification Search
None
See application file for complete search history.

(56) References Cited

U.S. PATENT DOCUMENTS

| 1,535,529 | A | 4/1925 | Hopkins |
| 2,454,541 | A | 11/1948 | Bock et al. |
| 3,341,418 | A | 9/1967 | Moses et al. |

(Continued)

FOREIGN PATENT DOCUMENTS

| AU | 701927 B2 | 6/1995 |
| CN | 102090393 A | 6/2011 |

(Continued)

OTHER PUBLICATIONS

"PH curves and indicators", retrieved from http://www.creative-chemistry.org.uk/alevel/module4/documents/N-ch4-05.pdf.*

(Continued)

*Primary Examiner* — Bethany P Barham
*Assistant Examiner* — Dominic Lazaro
(74) *Attorney, Agent, or Firm* — Stinson Leonard Street LLP

(57) ABSTRACT

An aqueous disinfectant solution comprising peroxyacetic acid; hydrogen peroxide; and a carbonate buffer is provided.

22 Claims, 1 Drawing Sheet

(56) References Cited

U.S. PATENT DOCUMENTS

| | | | |
|---|---|---|---|
| 3,488,287 A | 1/1970 | Seglin et al. | |
| 3,554,289 A | 1/1971 | Webb | |
| 3,708,431 A | 1/1973 | Prussin | |
| 4,051,059 A * | 9/1977 | Bowing | A01N 37/16 252/186.23 |
| 4,522,738 A | 6/1985 | Magid et al. | |
| 4,743,447 A | 5/1988 | Le Rouzic et al. | |
| 5,154,917 A | 10/1992 | Ibraham et al. | |
| 5,168,048 A | 12/1992 | Quax | |
| 5,269,959 A | 12/1993 | Schreibman | |
| 5,314,687 A | 5/1994 | Oakes et al. | |
| 5,344,652 A | 9/1994 | Hall, II et al. | |
| 5,480,575 A | 1/1996 | Altieri et al. | |
| 5,489,706 A | 2/1996 | Revell | |
| 5,545,374 A | 8/1996 | French et al. | |
| 5,643,862 A | 7/1997 | Jones et al. | |
| 5,656,302 A | 8/1997 | Cosentino et al. | |
| 5,804,546 A | 9/1998 | Hall | |
| 5,900,256 A * | 5/1999 | Scoville, Jr. | A01N 59/00 252/186.29 |
| 6,080,712 A | 6/2000 | Revell et al. | |
| 6,168,808 B1 | 1/2001 | Hamon Godin et al. | |
| 6,511,546 B1 | 1/2003 | Bivins et al. | |
| 6,514,509 B2 | 2/2003 | Tabasso | |
| 6,583,103 B1 | 6/2003 | Klinkhammer | |
| 6,589,565 B1 | 7/2003 | Richter et al. | |
| 6,699,828 B1 | 3/2004 | De Buzzaccarini et al. | |
| 6,726,936 B1 | 4/2004 | Asano et al. | |
| 6,767,874 B2 | 7/2004 | Gonzalez | |
| 7,056,536 B2 | 6/2006 | Richter et al. | |
| 7,189,385 B2 | 3/2007 | Montgomery | |
| 7,205,000 B2 | 4/2007 | Einziger | |
| 7,271,137 B2 | 9/2007 | Tucker et al. | |
| 8,012,411 B1 * | 9/2011 | Betty | A62D 3/38 422/306 |
| 8,377,421 B2 | 2/2013 | Giniger | |
| 8,546,120 B2 | 10/2013 | Dicosimo et al. | |
| 8,969,283 B2 | 3/2015 | Kaiser et al. | |
| 9,789,216 B2 * | 10/2017 | Berentsveig | A01N 37/16 |
| 2003/0129254 A1 * | 7/2003 | Yasuhara | A61K 31/19 424/601 |
| 2005/0036904 A1 | 2/2005 | Kajander et al. | |
| 2005/0282722 A1 | 12/2005 | McReynolds et al. | |
| 2006/0198797 A1 | 9/2006 | Giniger | |
| 2006/0204453 A1 | 9/2006 | Giniger | |
| 2006/0229226 A1 | 10/2006 | Giniger et al. | |
| 2007/0161243 A1 | 7/2007 | Mellies | |
| 2007/0166398 A1 * | 7/2007 | Bobbert | A01N 59/00 424/616 |
| 2007/0185000 A1 | 8/2007 | Zushi et al. | |
| 2007/0258915 A1 | 11/2007 | Kielbania | |
| 2009/0061017 A1 * | 3/2009 | Pedersen | A01N 37/16 424/616 |
| 2009/0285871 A1 | 11/2009 | Cunningham et al. | |
| 2009/0324508 A1 | 12/2009 | Bobbert | |
| 2010/0068295 A1 | 3/2010 | Bobbert | |
| 2010/0196503 A1 | 8/2010 | Heisig et al. | |
| 2010/0196505 A1 * | 8/2010 | Kaiser | A01N 37/16 424/616 |
| 2010/0227000 A1 | 9/2010 | Ames et al. | |
| 2010/0294987 A1 * | 11/2010 | Kater | A62D 3/38 252/186.42 |
| 2011/0081693 A1 | 4/2011 | Dicosimo et al. | |
| 2011/0085991 A1 | 4/2011 | Giniger | |
| 2012/0171301 A1 | 7/2012 | Koenig et al. | |
| 2012/0219636 A1 | 8/2012 | Li et al. | |

FOREIGN PATENT DOCUMENTS

| | | |
|---|---|---|
| CN | 102964285 A | 3/2013 |
| EP | 0745665 A2 | 12/1996 |
| EP | 0752466 A1 | 1/1997 |
| EP | 0733097 B1 | 10/1998 |
| EP | 1123655 A1 | 8/2001 |
| EP | 1829558 A1 | 9/2007 |
| EP | 1293215 B1 | 11/2007 |
| EP | 2436265 A2 | 4/2012 |
| GB | 2293157 A | 3/1996 |
| JP | 2003-292996 A | 10/2003 |
| JP | 2004-285154 A | 10/2004 |
| JP | 2011-121912 A | 6/2011 |
| WO | 8808667 A1 | 11/1988 |
| WO | 9116435 A1 | 10/1991 |
| WO | 9414321 A1 | 7/1994 |
| WO | 9516023 A1 | 6/1995 |
| WO | 1996019558 A1 | 6/1996 |
| WO | 98/11777 A1 | 3/1998 |
| WO | 9833880 A1 | 8/1998 |
| WO | 9837762 A1 | 9/1998 |
| WO | 9846715 A1 | 10/1998 |
| WO | 2000078153 A1 | 12/2000 |
| WO | 2005055963 A2 | 6/2005 |
| WO | 2006016145 A1 | 2/2006 |
| WO | 2006089139 A2 | 8/2006 |
| WO | 2007051957 A1 | 5/2007 |
| WO | 2007/080187 A1 | 7/2007 |
| WO | 2008/033206 A1 | 3/2008 |
| WO | 2008140974 A1 | 11/2008 |
| WO | 2009027857 A1 | 3/2009 |
| WO | 2009064856 A1 | 5/2009 |
| WO | 2009/118714 A2 | 10/2009 |
| WO | 2010102188 A1 | 9/2010 |
| WO | 2011/008225 A2 | 1/2011 |
| WO | 2012021520 A1 | 2/2012 |
| WO | 2012128734 A1 | 9/2012 |
| WO | 2013096814 A1 | 6/2013 |
| WO | 2013185074 A2 | 12/2013 |

OTHER PUBLICATIONS

English Abstract of KR1020080098157A with EPO Machine Translation, 13 pages.

Multitrope (aka Monafax) 1214 MSDS; downloaded Aug. 27, 2015, 1 page.

Genapol EP 2564 MSDS Product Data Sheet; Clariant; downloaded Aug. 27, 2015, 2 pages.

Triton X-100 Surfactant, Product Information Sheet, The Dow Chemical Company, Form No. 119-01882-1207, 2 pages.

Silocone Antifoams, Antifoam 86/103, Basildon Chemicals, http://www.baschem.co.uk/products/product-type/silicone-antifoams/antifoam-86013/[Sep. 12, 2013 3:52:37 PM], 2 pages.

International Search Report dated Mar. 13, 2015 in PCT/AU2013/001463, 4 pages.

Written Opinion dated Mar. 13, 2015 in PCT/AU2013/001463, 9 pages.

The Merck Index, Encyclopedia of Chemicals, Drugs and Biologicals, 6601. Octoxynol, Windholz et al., Eds., Tenth Edition, Copyright 1983, 4 pages.

TRITON X-100, Product Information Sheet, Sigma-Aldrich, Apr. 21, 1999, 2 pages.

Chemical Abstracts, vol. 101, No. 4, Jul. 23, 1984, p. 102, No. 25407e, Columbus, Ohio US; Kasei K.K.: "Sprayable Foaming Cleaning Compositions" & Jpn. Kokai Tokkyo Koha JP 58,191,800/83,191,8007, 1 page.

Japanese Patent Office Machine Translation of JPS58-191800A, 4 pages.

Japanese Patent Office Machine Translation of JPS59-66499A, 9 pages.

* cited by examiner

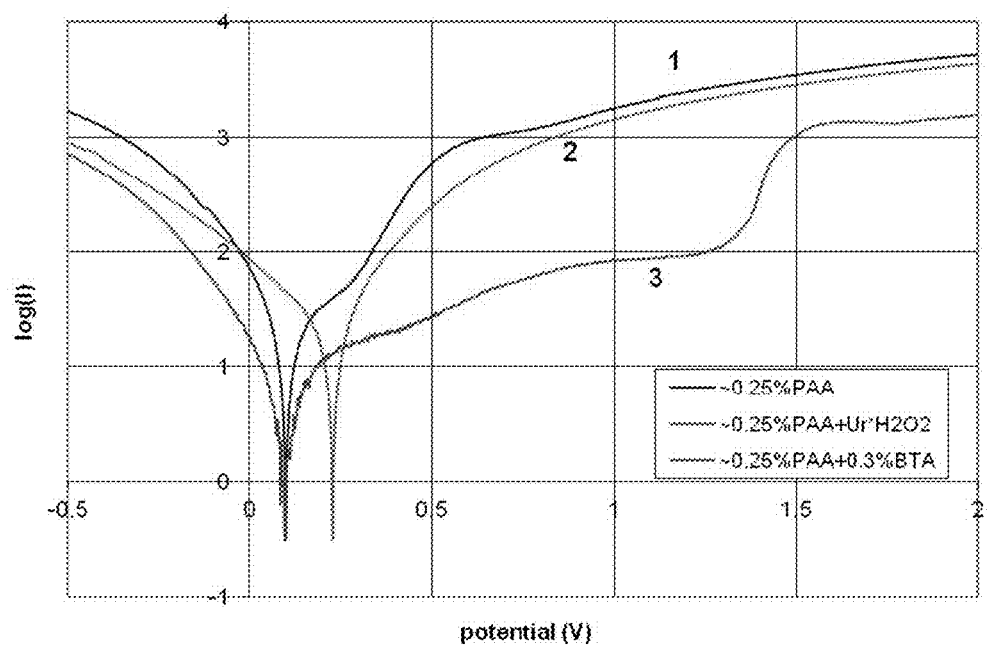

DISINFECTANT

FIELD OF THE INVENTION

The present invention relates to compositions suitable for use in disinfecting or sterilizing instruments, exposed surfaces or spaces which may be infected with bacteria, fungi, viruses, fungal or bacterial spores, prions, and the like.

BACKGROUND

Any discussion of the prior art throughout the specification should in no way be considered as an admission that such prior art is widely known or forms part of common general knowledge in the field.

BACKGROUND OF THE INVENTION

"Sterilization" has been defined as the process of destroying all microorganisms, spores and their pathogenic products. A 6 log reduction in the amount of such pathogens is generally required to provide a suitable sterility assurance level. "Disinfection" is a similar process, the difference being that it results in a lesser degree of biocidal effect, particularly on bacterial spores. Disinfection is thus easier to achieve than sterilization.

Sterilants or disinfectants are usually liquids and can be applied to articles requiring disinfection or sterilization in a variety of ways. In recent years, the use gas or aerosol dispensing technologies to dispense sterilants or disinfectants has become widespread. Gas or aerosol processes are particularly attractive since they reduce the amount of liquid sterilant or disinfectant used. The primary benefit of using micro volumes of liquid is that rising steps can sometimes be eliminated and drying times are often significantly reduced compared to using say, soaking baths. This shortened cycle time reduces the turnaround time for any given instrument which in turn translates into a much smaller capital outlay is tied up in instruments.

Gas or aerosol processes also tend to be conducted in closed systems, which means that operator safety is also enhanced relative to conventional methods that expose workers to large volumes of open sterilant or disinfectant solutions.

Aerosol based approaches in which nebulisation takes place by ultrasonication of a bulk liquid are known and are a particularly good way to achieve high sterilization efficacies using micro volumes of sterilant.

In recent years there has been a marked increase in the number, variety and levels of resistance of micro-organisms which have been identified as particularly problematic in hospital and medical environments. The use of hydrogen peroxide or peroxyacetic acid as a disinfectant has become greatly preferred in that time. Prior to the 1990s these peroxides were considered too unstable and hazardous to be used.

Peroxyacetic acid is particularly effective against microorganisms. It is a very broad spectrum germicidal agent, effective against both gram negative and gram positive bacteria, fungi and yeasts and viruses under suitable conditions. It is also considered to be sporicidal. It is efficacious in low concentrations and it remains highly effective even in the presence of relatively high organic loads. The decomposition products of peroxyacetic acid, namely acetic acid, water and oxygen are also environmentally friendly.

Peroxyacetic acid is advantageous over hydrogen peroxide, since, unlike hydrogen peroxide it is not deactivated by microorganisms' catalase or peroxidase. There is also little or no habituation of microorganisms to peroxyacetic acid.

Aqueous peroxyacetic acid solutions are commercially available. Peroxyacetic acid typically exists in equilibrated aqueous mixtures of hydrogen peroxide and acetic acid as represented by the following equation:

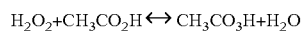

$$H_2O_2 + CH_3CO_2H \leftrightarrow CH_3CO_3H + H_2O$$

One example of such a commercially available peroxyacetic acid solution is Proxitan from Solvay which contains approximately 5% peroxyacetic acid, 7.5% acetic acid and 24% $H_2O_2$. These amounts typify the ratios found in such equilibrated mixtures, namely peroxyacetic acid:acetic acid:hydrogen peroxide in a ratio of 1:1.5:5.

Peroxyacetic acid solutions are quite acidic and are highly corrosive. When using these in the field of sterilization it is usually necessary to add a buffering component to reduce pH to reduce corrosion and to produce a much more generally physiologically acceptable pHs. Phosphate buffers are typically used for this purpose.

It is an object of the present invention to overcome or ameliorate at least one of the disadvantages of the prior art, or to provide a useful alternative.

SUMMARY

According to a first aspect the invention provides an aqueous disinfectant solution comprising:
peroxyacetic acid;
hydrogen peroxide; and
a carbonate buffer Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Preferably the concentration of peroxyacetic acid is greater than 0.1 wt %, although in alternative embodiments is can be greater than 0.15 wt % or greater than 0.2 wt %. It is generally preferred if the amount of peroxyacetic acid is 0.10 to 0.30 wt %.

Preferably the ratio of hydrogen peroxide:peroxyacetic acid is 5:1 or greater, although in alternative embodiments the ratio of hydrogen peroxide:peroxyacetic acid is 10:1 or greater, 15:1 or greater; or even 30:1 or greater.

Preferably the carbonate buffer comprises hydrogen carbonate anions and hydroxide anions or hydrogen carbonate anions and carbonate anions.

Preferably, the amount of carbonate buffer is chosen so as to provide a pH of between 5 to 7.

The disinfectant solution may, for preference, include a surfactant, preferably a non-ionic surfactant. The surfactant may be selected from the group consisting of polyoxyethylene alkyl ether phosphates, (polyethylene glycol p-(1,1,3,3-tetramethylbutyl)-phenyl ether) and cocoamidopropylamino oxide.

A particularly preferred class of surfactants are phosphate based anionic surfactants, particularly polyoxyethylene alkyl ether phosphates, such as those sold by Croda under the trade name Monafax M1214 or Multitrope 1214

The disinfectant solution may, for preference include a corrosion inhibitor, such as a benzotriazole or urea.

The disinfectant solution may, for preference include an antifoaming agent.

According to a second aspect the invention provides a method of disinfection of an article comprising contacting the article with an aqueous disinfectant solution according to the first aspect.

Preferably the method is carried out in a temperature range of from 15-40° C., more preferably from 20-35° C. and most preferably at ambient temperature.

In buffers comprising hydrogen carbonate anions and hydroxide anions, the molar ratio of hydrogen carbonate: hydroxide is about 0.9:1 to about 1.1:1, more preferably about 1:1. In the preferred sodium salt form, the w:w ratio of hydrogen carbonate:hydroxide is from about 2.5:1 to 2:1, more preferably about 2.3:1, or the ratio of carbonate: hydroxide is from about 2.9:1 to 2.4:1, more preferably about 2.65:1.

In buffers comprising hydrogen carbonate anions and carbonate anions, the molar ratio of hydrogen carbonate: carbonate is about 0.15:1 to about 0.25:1, more preferably about 0.18:1. In the preferred sodium salt form, the w:w ratio of hydrogen carbonate:carbonate is from about 0.1:1 to about 0.2:1, more preferably about 0.14:1.

Although the term "buffer" is used, it is important to understand that the carbonate components need not form a true buffer system—it was found to be adequate just to use the carbonate components as pH adjusters. The important consideration is the adjustment of the 0.1-0.3 wt % peroxyacetic acid to a pH of between 6.3 and 6.8 in the final working solution (at which pH hydrogen carbonate will be the dominant buffering or pH controlling species).

The time required is preferably that to achieve a resultant load on microorganisms that is acceptable for the intended use of the article. Put alternatively, the time required by the aqueous disinfectant of the present invention to achieve a 6 log reduction in microorganism load at room temperature is preferably less than 5 minutes, or even more preferably less than 4 minutes.

The present invention is applicable both to the disinfection or sterilization of instruments and articles placed in small disinfection chambers, biological safety cabinets, isolators, glove boxes, incubators, materials airlocks and the like. The invention is also applicable for disinfection or sterilization of food containers or the like and manufacturing machinery and is also applicable for the disinfection of very large spaces.

BRIEF DESCRIPTION OF THE DRAWINGS

FIG. 1 shows the effect of urea on corrosion inhibition.

DESCRIPTION

Peroxyacetic acid is generated by the addition of acetic acid to a peroxidising agent such as hydrogen peroxide or a peroxy salt. The most common and inexpensive method used to generate peroxyacetic acid is to use a combination of acetic acid and aqueous hydrogen peroxide, in which case the peroxyacetic acid is in equilibrium with a number of other species as shown:

$$H_2O_2 + CH_3CO_2H \leftrightarrow CH_3CO_3H + H_2O$$

As mentioned, the native ratios found in such equilibrated mixtures typically provide peroxyacetic acid:acetic acid: hydrogen peroxide in a ratio of 1:1.5:5. That is, the ratio of the active disinfectant species, peroxyacetic acid and hydrogen peroxide, in such systems is typically around 1:5.

Peroxyacetic acid can also be generated from solid peroxide precursors such as sodium perborate, sodium percarbonate, carbamide peroxide (urea peroxide) or potassium fluoride peroxosolvate in combination with acetic acid to generate peroxyacetic acid. Although slightly more expensive than the acetic acid/hydrogen peroxide approach, these sources of peroxyacetic acid are seen as desirable since they do not include large amounts of hydrogen peroxide, which is regarded as a less potent biocide than peroxyacetic acid.

In some cases, solid peroxide precursors can be used in combination with hydrogen peroxide/acetic acid systems.

Regardless of how it is produced, the pH of peroxyacetic acid is very low, around 2.8. Such a low pH means that it is highly corrosive. Such a low pH is also fundamentally incompatible with systems that are to be used in intimate contact with patients. This means that in order to be used in sensitive medical instruments, the pH must thus be controlled by way of a buffer. An ideal pH range that will result in minimal corrosion with maximum compatibility for human contact is between about pH 5.5 and pH 7.

Typically, phosphate buffers have been used to control pH of peroxyacetic acid systems. However, other common bases, such as hydroxide or carbonate, have also been used to adjust the pH of peroxyacetic acid.

Surprisingly, the present applicant has found that the biocidal activity of peroxyacetic acid, even against spores, above a certain concentration (about 0.2 wt %) can be potentiated in the presence of a combination of a carbonate buffer and excess hydrogen peroxide (typically 5 times by weight of the peroxyacetic acid or more).

These results are surprising for two reasons. Firstly, it appears counterintuitive that, under any circumstances, the addition of hydrogen peroxide, a weaker biocide than peroxyacetic acid, could actually increase the efficacy of biocidal activity. Secondly, it was not previously observed that the nature of the buffer was in any way relevant to the biocidal activity of the sterilants.

Those skilled in the art will appreciate that the carbonate/ hydrogen carbonate/hydroxide chemical system is dominated by various equilibria, namely firstly the dissociation of dissolved $CO_2$ (written as carbonic acid)

$$H_2CO_3 \leftrightarrow HCO_3^- + H^+$$

which has a pKa of 6.37, and secondly the dissociation of hydrogen carbonate to carbonate $$HCO_3^- \leftrightarrow CO_3^{2-} + H^+$$

which has a pKa of 10.33. Thus, between pH 6.37 and pH 10.33, the predominant species is $HCO_3^-$. Below pH 6.37, dissolved $CO_2$ predominates, and above pH 10.33, carbonate predominates. So, in the case of the present invention, the predominant buffer species at the preferred pH range, about 6.5, is hydrogencarbonate.

Clearly, in the presence of acidic species such as peroxyacetic acid and acetic acid, as are found in the present invention, of hydroxide ($OH^-$) that may be used in the carbonate buffer of the present invention, the equilibria will shift dynamically depending upon the amounts of all those species present.

The hydrogen carbonate ($HCO_3^-$) and carbonate anions ($CO_3^{2-}$) and/or hydroxide anions ($OH^-$) in the buffer are ideally present in equimolar amounts or close to equimolar amounts. They would normally be provided in the form of their respective sodium or potassium salts but any suitable cationic counter ion can be present.

It has been found that the buffer is most advantageously added in an amount to keep the pH between 5.5 and pH 7 and if possible around 6-6.5. The addition of amounts of buffer below these amounts causes corrosion problems whereas the addition of too much buffer, towards slightly basic conditions, reduces the efficacy of the combination.

The above equation illustrates one equilibrium equation involving peroxyacetic acid and the present invention functions well using such equilibrated mixtures alone.

However, it has been found that adding excess hydrogen peroxide solution enhances biocidal efficacy and can contribute as much as 1 or 2 log reduction in microbial load, i.e. a 10-fold or 100-fold increase in efficacy.

Additionally, it was found that the presence of a surfactant can also increase the biocidal efficacy of such disinfectant solutions. A particularly preferred class of surfactants which gave improved performance were phosphate based anionic surfactants, particularly polyoxyethylene alkyl ether phosphates, such as those sold by Croda under the trade name Monafax M1214 or Multitrope 1214. The addition of Triton X-100 (polyethylene glycol p-(1,1,3,3-tetramethylbutyl)-phenyl ether) and/or cocoamidopropylamino oxide was shown to give some improvement in performance relative to systems without such additives.

Although the disinfectant solutions of the present invention operate successfully at pH's between about 5.5 and 6.5, such a pH can still be corrosive. It was found that the buffer systems of the present invention continued to work well in the presence of added corrosion inhibitors. Urea was found to be a particularly suitable corrosion inhibitor as were the H-1,2,4-benzotriazole family. These could be used up to their normal corrosion inhibiting compositions, e.g. copper could be protected by the addition of benzotriazoles up to 0.3%.

Urea is particularly suited as it can be added in the form of carbamate peroxide which is a complex of urea and hydrogen peroxide. This compound is a stable solid and can be included with the buffering components prior to mixing with the acetic acid or it can be added as a separate component. Upon dissolution in water, carbamate peroxide produces urea and hydrogen peroxide, so it produces both urea to function as a corrosion inhibitor and hydrogen peroxide as required by the present biocidal compositions.

EXAMPLES

Formulation

The disinfectants of the present invention may advantageously be prepared as multi component systems. A typical example is set out herein. Component A is the peroxyacetic acid solution and component B is the buffer. Additional hydrogen peroxide can be introduced with or as part of component A, or after A and B have been mixed, for example.

Component A contained peroxyacetic acid (approx 5%), acetic acid (approximately 7.5%), and hydrogen peroxide (approximately 25%), with the balance being water. The total volume was around 40 ml.

56.3 g of 35% $H_2O_2$ was added to component A to ensure an excess of hydrogen peroxide This mixture was then diluted by to a total volume of 1 l.

Component B, the buffer component, contained 2.9 g of $NaHCO_3$ (0.03 moles), 1.24 g (0.03 moles) of NaOH and 0.6 g of the surfactant Triton X-100 (or a similar suitable amount of Monafax). Component B was added to the 1 l working solution.

An alternative buffer component B contained 4.5 g of $Na_2CO3$ (0.042 moles) and 0.63 g NaHCO3 (0.0075 moles) and 0.6 g of the surfactant Triton X-100 (or a similar suitable amount of Monafax). This component B could also likewise be added to the 1 l working solution.

The resultant working solution had a volume of 1 l, a peroxyacetic acid concentration of around 0.20%, a hydrogen peroxide concentration of around 3.08% and a pH of 6.26 Those figures are within the most desired range of peroxyacetic acid concentrations (0.1 to 0.3%) and pH's (5.3 to 6.3).

Starting Components A and B are expected to be stable for 3-4 years, however, the buffered solution should be used within 8 hrs of mixing.

Test Method

The test method employed and described below is typical of all the test methodology used in the present invention to determine biological loads.

The working solution was tested against spores of *Bacillus subtilis* ATCC 19659 at room temperature. Media was TSB+1% Na-thiosulfate+10% Tween 80+1 ml Catalase.

The test method involved taking a 9 ml sample and adding 1 ml culture (with 5% horse serum) and then incubating at the desired temperature if necessary. 1 ml of the incubated sample was then removed at each time point and neutralized with 9 ml neutralizer. The resultant was diluted with saline, plated out and the plates incubated at 37° C. for 48 hr. The results were then able to be expressed in terms of a log reduction. As is usual in the art, a log reduction is a $log_{10}$ reduction. A 4 log reduction means 1 in $10^4$ organisms survived, 5 log corresponds to 1 in $10^5$ organisms surviving and so on. High level disinfection is widely defined and understood as a reduction of 6 log or greater, than is, no more than 1 in 1,000,000 microorganisms survives the process.

Example 1

Table 1 provides a comparative example showing the effect of various buffers on the efficacy of peroxyacetic acid systems without excess hydrogen peroxide. The concentration of the composition was otherwise held constant, and in all cases the pH was kept as close to constant as possible using the requisite amount of buffer. Thus, the only difference between the formulations was the nature and amount of the buffer required to achieve a given pH.

The amount of hydrogen peroxide present was around 1%, and so was thus around 5 times the amount by weight of peroxyacetic acid used. Composition I used a conventional phosphate buffer and composition II used a hydroxide buffer whereas composition III and IV used carbonate buffers prepared from various starting components. In all cases, the nature of the buffer did not appear to produce any meaningful effect on biocidal activity. If anything, the carbonate buffers performed slightly worse than the phosphate buffer.

Example 2. Effect of Excess Hydrogen Peroxide

Table 2 shows the results of the addition of hydrogen peroxide in excess of the amount present in Table 1, such that the ratio of hydrogen peroxide:peroxyacetic acid was changed to be around 15:1. All other elements of the procedure remained the same.

The results were dramatically different depending on the buffer used. The addition of excess hydrogen peroxide in the case of phosphate and hydroxide buffers produced little or no meaningful effect, however, in the compositions of the present invention which used carbonate buffers, the reduction in microorganisms rose to 6.4 log, that is, the addition of excess hydrogen peroxide alone resulted in a tenfold increase in biocidal activity with carbonate buffer.

The results in the case of phosphate and hydroxide buffers are largely as expected—the addition of hydrogen peroxide, which is a weaker biocide than peroxyacetic acid, did not result in any significant effect on biocidal activity. However, unexpectedly, the addition of hydrogen peroxide in excess of a ratio of 5:1 with respect to peroxyacetic acid did, in the case where carbonate buffers were used, result in a significant synergistic effect.

The potentiation was thus not observable at ratios of hydrogen peroxide:peroxyacetic acid of 5:1, however, at hydrogen peroxide:peroxyacetic acid ratios of 15:1, the result was clearly visible. It is believed that the results become observable at ratios of 10:1. It is most likely that the results commence where the hydrogen peroxide:peroxyacetic acid ratio are between 5:1 and 10:1.

Example 3 Microorganisms

Table 3 shows the effect of added hydrogen peroxide against a variety of organisms. For compositions I and Ia, and II and IIa, the effect is not readily demonstrated since the compositions either with or without excess hydrogen peroxide were so efficacious that total kill (7.1 log reduction for *Staphylococcus aureus* and 8.3 log reduction for *Candida albicans*) was achieved in 1 minute or less. However, the results demonstrate that for bacteria that were not completely eliminated in less than 1 minute, *Aspergillus niger* and *Bacillus subtilis*, there was a significant difference (100-fold and 10-fold respectively) observed when the amount of hydrogen peroxide was increased.

Example 4—Minimum Peroxyacetic Acid Concentration

The above results were for a constant peroxyacetic acid concentration of 0.2%. Table 4 shows the minimum levels of concentration of peroxyacetic acid required to exhibit potentiation. Compositions I and II, which had a peroxyacetic acid composition of 0.2%, exhibited the synergy shown above, with excess hydrogen peroxide giving rise to a 100-fold increase in efficacy.

Reducing the amount of peroxyacetic acid by a quarter, to 0.15 wt %, and adding a similar excess of hydrogen peroxide as shown in composition III gives a result that is broadly in line with the result obtained for the higher amount of peroxyacetic acid, but without hydrogen peroxide. This result indicates that, when a carbonate buffer is used, a portion of the peroxy acetic acid can be removed (resulting in a less corrosive composition) and replaced by hydrogen peroxide, with the resultant synergy meaning there is little or no loss of overall biocidal efficacy.

Further reducing the amount of peroxyacetic acid, by half, to 0.1 wt %, showed a significant decrease in efficacy. The minimum efficacious amount of peroxy acetic acid is thus between 0.0 and 0.15 wt %.

Example 5—Effect of Excess Hydrogen Peroxide

Table 5 shows the effect of the amount of additional hydrogen peroxide added. Composition I has 5:1 hydrogen peroxide:peracetic acid, which is considered to be the level at which the buffer exerts no synergistic effect on the mixture. Composition II shows the addition of hydrogen peroxide, such that the ratio is 3%:0.22%, or about 15:1. This shows the increase in biocidal effect enabled by the carbonate buffer. The effect is moderate after 3 minutes but clearly distinct after 4 minutes. Composition II shows a much higher excess of hydrogen peroxide, 7%:0.22%, or about 31:1. The synergy is clearly still present and shows an increasing effect with increasing amounts of hydrogen peroxide. The comparison of values for compositions II and III at 4 minutes is not so meaningful, since complete kill has been achieved, but the results at 3 minutes show that at even at a ratio of 32:1 hydrogen peroxide:peroxyacetic acid the synergistic enhancement caused by the carbonate buffer can be observed.

Example 6 Effect of Temperature and Hydrogen Peroxide Source

As indicated, the source of hydrogen peroxide need not be a hydrogen peroxide solution. Urea peroxide is a particularly attractive option since it can produce urea, which has a corrosion inhibition effect, as well as hydrogen peroxide, and is also easily handled.

Table 6 shows the effect of the carbonate buffers when the hydrogen peroxide was presented as a urea/hydrogen peroxide complex. The amount used was chosen so as to produce a 3 wt % concentration of hydrogen peroxide, to be compatible with other results. The data show that the methods and compositions of the present invention function independently of the source of hydrogen peroxide.

In addition, the results show that, as expected, increasing temperature reduces kill time. Composition II was the same as Composition I with the exception that the exposure to the composition took place at 35° C. instead of 20° C. At 35° C., the time to total kill (5.5 log reduction), was reduced to 3 minutes or less, as compared to around 5 minutes at 20° C.

FIG. 1 shows the effect of urea on corrosion inhibition—the corrosion potential in the presence of urea becomes more positive; indicating a less corrosive effect on metals would result.

The pH's of the buffered solutions of the present invention mean that corrosion is less likely to become a problem, and they present solutions could be used for example with a variety of metal fittings such as copper or aluminium. However, if desired, corrosion inhibitors can be added since it has been found that the use of corrosion inhibitors does not adversely affect the performance of the buffered solutions. Suitable corrosion inhibitors tested include urea or H1,2,4-benzotriazol (0.3%). Urea peroxide is an example of a compound that can be used as a peroxidising agent for acetic acid which also has the benefit of releasing urea into the solution which is a corrosion inhibitor.

Example 7 Effect of Surfactant

Table 7 shows the effect of a surfactant, Monafax M1214 upon the present invention. It can be seen that the presence of Monafax significantly enhanced the biocidal effect of the present invention. 0.1% Monafax let to a 0.7 log increase. A much higher amount, 0.38%, of Monafax gave some further increased benefit also. Monafax is a polyoxyethylene alkyl ether phosphates. Other surfactants preferably non-ionic surfactant such as triton x (polyethylene glycol p-(1,1,3,3-tetramethylbutyl)-phenyl ether) or cocoamidopropylamino oxide have been shown to not have a detrimental effect on the compositions of the present invention.

Example 8 Effect of Additives

Table 8 shows the effect of combinations of surfactant and corrosion inhibitor. None of these appeared to interfere with the synergistic effect exhibited as a result of the combination of peroxyacetic acid, excess hydrogen peroxide and carbonate buffer.

Example 9 Antifoaming Agent

One practical requirement of importance is that the compositions used for disinfection are resistant to foaming, which can severely inhibit processing options. The mixtures of the present invention were further tested with antifoaming components. Again, it could be seen that the synergistic effect exhibited as a result of the combination of peroxyacetic acid, excess hydrogen peroxide and carbonate buffer was not affected.

TABLE 1

Sporicidal efficacy of biocides on the base of peroxyacetic acid against *Bacillus subtilis* spores (ATCC 19659) at room temperature.

| Composition | Ingredient | Wt % of ingredient | pH | Exposure time (min) | Log reduction |
|---|---|---|---|---|---|
| I | peroxyacetic acid | 0.2 | 6.44 | 4 | 5.82 |
|  | acetic acid | 0.3 |  |  |  |
|  | H2O2 | 1 |  |  |  |
|  | Triton X-100 | 0.1 |  |  |  |
|  | Cocamine oxide | 0.1 |  |  |  |
|  | phosphate buffer |  |  |  |  |
| II | peroxyacetic acid | 0.2 |  |  |  |
|  | acetic acid | 0.3 | 6.45 | 4 | 5.48 |
|  | H2O2 | 1 |  |  |  |
|  | Triton X-100 | 0.1 |  |  |  |
|  | Cocamine oxide | 0.1 |  |  |  |
|  | basic buffer (NaOH) |  |  |  |  |
| III | peroxyacetic acid | 0.2 | 6.49 | 4 | 5.28 |
|  | acetic acid | 0.3 |  |  |  |
|  | H2O2 | 1 |  |  |  |
|  | Triton X-100 | 0.1 |  |  |  |
|  | Cocamine oxide | 0.1 |  |  |  |
|  | carbonate buffer I |  |  |  |  |
|  | (NaHCO$_3$ + NaOH) |  |  |  |  |
| IV | peroxyacetic acid | 0.2 | 6.44 | 4 | 5.40 |
|  | acetic acid | 0.3 |  |  |  |
|  | H2O2 | 1 |  |  |  |
|  | Triton X-100 | 0.1 |  |  |  |
|  | Cocamine oxide | 0.1 |  |  |  |
|  | carbonate buffer II |  |  |  |  |
|  | (Na$_2$CO$_3$ + NaHCO$_3$) |  |  |  |  |

TABLE 2

Sporicidal efficacy of biocides on the base of peroxyacetic acid with excess of hydrogen peroxide against *Bacillus subtilis* spores (ATCC 19659) at room temperature

| Composition | Ingredient | Wt % of ingredient | pH | Exposure time (min) | Log reduction |
|---|---|---|---|---|---|
| I | peroxyacetic acid | 0.2 | 6.42 | 4 | 5.5 |
|  | acetic acid | 0.3 |  |  |  |
|  | H2O2 | ~3.0 |  |  |  |
|  | Triton X-100 | 0.1 |  |  |  |
|  | Cocamine oxide | 0.1 |  |  |  |
|  | phosphate buffer |  |  |  |  |
| II | peroxyacetic acid | 0.2 |  |  |  |
|  | acetic acid | 0.3 | 6.50 | 4 | 5.9 |
|  | H2O2 | ~3.0 |  |  |  |
|  | Triton X-100 | 0.1 |  |  |  |
|  | Cocamine oxide | 0.1 |  |  |  |
|  | basic buffer (NaOH) |  |  |  |  |
| III | peroxyacetic acid | 0.2 | 6.40 | 4 | 6.4 |
|  | acetic acid | 0.3 |  |  |  |
|  | H2O2 | ~3.0 |  |  |  |
|  | Triton X-100 | 0.1 |  |  |  |
|  | Cocamine oxide | 0.1 |  |  |  |
|  | carbonate buffer I |  |  |  |  |
|  | (NaHCO$_3$ + NaOH) |  |  |  |  |
| IV | peroxyacetic acid | 0.2 | 6.42 | 4 | 6.4 |
|  | acetic acid | 0.3 |  |  |  |
|  | H2O2 | ~3.0 |  |  |  |
|  | Triton X-100 | 0.1 |  |  |  |
|  | Cocamine oxide | 0.1 |  |  |  |
|  | carbonate buffer II |  |  |  |  |
|  | (Na2CO$_3$ + NaHCO$_3$) |  |  |  |  |

TABLE 3

Biocidal efficacy of solution on the base of peroxyacetic acid with excess of hydrogen peroxide at room temperature

| Composition | Ingredient | Wt % of ingredient | pH | Test organisms | Exposure time (min) | Log reduction |
|---|---|---|---|---|---|---|
| I | peroxyacetic acid | 0.2 | 6.09 | *Staphylococcus* | 0.5 | 7.1 |
|  | acetic acid | 0.3 |  | *aureus* |  |  |
|  | H2O2 | ~1.0 |  | ATCC 6538 |  |  |
|  | Triton X-100 | 0.1 |  | (No = 1.32E+8) |  |  |
|  | Cocamine oxide | 0.1 |  |  |  |  |
|  | carbonate buffer I |  |  |  |  |  |
| Ia | peroxyacetic acid | 0.2 | 5.89 | *Staphylococcus* | 0.5 | 7.1 |
|  | acetic acid | 0.3 |  | *aureus* |  |  |
|  | H2O2 | ~3.0 |  | ATCC 6538 |  |  |
|  | Triton X-100 | 0.1 |  | (No = 1.32E+8) |  |  |
|  | Cocamine oxide | 0.1 |  |  |  |  |
|  | carbonate buffer I |  |  |  |  |  |
| II | peroxyacetic acid | 0.2 | 6.09 | *Candida* | 1 | 8.3 |
|  | acetic acid | 0.3 |  | *albicans* |  |  |
|  | H2O2 | ~1.0 |  | ATCC 10231 |  |  |
|  | Triton X-100 | 0.1 |  | (No = 1.91E+8) |  |  |
|  | Cocamine oxide | 0.1 |  |  |  |  |
|  | carbonate buffer I |  |  |  |  |  |
| IIa | peroxyacetic acid | 0.2 | 5.89 | *Candida* | 1 | 8.3 |
|  | acetic acid | 0.3 |  | *albicans* |  |  |
|  | H2O2 | ~3.0 |  | ATCC 10231 |  |  |

TABLE 3-continued

Biocidal efficacy of solution on the base of peroxyacetic acid with excess of hydrogen peroxide at room temperature

| Composition | Ingredient | Wt % of ingredient | pH | Test organisms | Exposure time (min) | Log reduction |
|---|---|---|---|---|---|---|
|  | Triton X-100 | 0.1 |  | (No = 1.91E+8) |  |  |
|  | Cocamine oxide | 0.1 |  |  |  |  |
|  | carbonate buffer I |  |  |  |  |  |
| III | peroxyacetic acid | 0.2 | 6.09 | *Aspergillus* | 1 | 4.4 |
|  | acetic acid | 0.3 |  | *niger* |  |  |
|  | H2O2 | ~1.0 |  | ATCC 16404 |  |  |
|  | Triton X-100 | 0.1 |  | (No = 2.75E+7) |  |  |
|  | Cocamine oxide | 0.1 |  |  |  |  |
|  | carbonate buffer I |  |  |  |  |  |
| IIIa | peroxyacetic acid | 0.2 | 5.89 | *Aspergillus* | 1 | 6.4 |
|  | acetic acid | 0.3 |  | *niger* |  |  |
|  | H2O2 | ~3.0 |  | ATCC 16404 |  |  |
|  | Triton X-100 | 0.1 |  | (No = 2.75E+7) |  |  |
|  | Cocamine oxide | 0.1 |  |  |  |  |
|  | carbonate buffer I |  |  |  |  |  |
| IV | peroxyacetic acid | 0.2 | 6.09 | *Bacillus* | 4 | 5.4 |
|  | acetic acid | 0.3 |  | *subtilis* |  |  |
|  | H2O2 | ~1.0 |  | ATCC 19659 |  |  |
|  | Triton X-100 | 0.1 |  | (No = 2.75E+7) |  |  |
|  | Cocamine oxide | 0.1 |  |  |  |  |
|  | carbonate buffer I |  |  |  |  |  |
| IVa | peroxyacetic acid | 0.2 | 5.89 | *Bacillus* | 4 | 6.5 |
|  | acetic acid | 0.3 |  | *subtilis* |  |  |
|  | H2O2 | ~3.0 |  | ATCC 19659 |  |  |
|  | Triton X-100 | 0.1 |  | (No = 2.75E+7) |  |  |
|  | Cocamine oxide | 0.1 |  |  |  |  |
|  | carbonate buffer I |  |  |  |  |  |

TABLE 4

Sporicidal efficacy of biocides on the base of different concentration of peroxyacetic acid against *Bacillus subtilis* spores (ATCC 19659) at room temperature

| Composition | Ingredient | Wt % of ingredient | pH | Exposure time (min) | Log reduction |
|---|---|---|---|---|---|
| I | peroxyacetic acid | 0.2 | 6.82 | 5 | 5.1 |
|  | acetic acid | 0.3 |  |  |  |
|  | H2O2 | 1 |  |  |  |
|  | Triton X-100 | 0.1 |  |  |  |
|  | Cocamine oxide | 0.1 |  |  |  |
|  | carbonate buffer I |  |  |  |  |
| II | peroxyacetic acid | 0.2 |  |  |  |
|  | acetic acid | 0.3 | 6.54 | 5 | 7.1 |
|  | H2O2 | ~3.0 |  |  |  |
|  | Triton X-100 | 0.1 |  |  |  |
|  | Cocamine oxide | 0.1 |  |  |  |
|  | carbonate buffer I |  |  |  |  |
| III | peroxyacetic acid | 0.15 | 6.71 | 5 | 4.8 |
|  | acetic acid | 0.23 |  |  |  |
|  | H2O2 | ~3.0 |  |  |  |
|  | Triton X-100 | 0.1 |  |  |  |
|  | Cocamine oxide | 0.1 |  |  |  |
|  | carbonate buffer I |  |  |  |  |
| IV | peroxyacetic acid | 0.1 | 6.7 | 5 | 2.7 |
|  | acetic acid | 0.15 |  |  |  |
|  | H2O2 | ~3.0 |  |  |  |
|  | Triton X-100 | 0.1 |  |  |  |
|  | Cocamine oxide | 0.1 |  |  |  |
|  | carbonate buffer I |  |  |  |  |

TABLE 5

Sporicidal efficacy of biocides on the base of peroxyacetic acid with different excess of hydrogen peroxide against *Bacillus subtilis* spores (ATCC 19659) at room temperature

| Composition | Ingredient | Wt % of ingredient | pH | Exposure time (min) | Log reduction |
|---|---|---|---|---|---|
| I | peroxyacetic acid | 0.22 | 6.7 | 3 | 2.5 |
|  | acetic acid | 0.3 |  |  |  |
|  | H2O2 | ~1.0 |  | 4 | 4.2 |
|  | Triton X-100 | 0.1 |  |  |  |
|  | Cocamine oxide | 0.1 |  |  |  |
|  | Carbonate buffer |  |  |  |  |
| II | peroxyacetic acid | 0.22 |  |  |  |
|  | acetic acid | 0.3 | 6.57 | 3 | 3.1 |
|  | H2O2 | ~3.0 |  |  |  |
|  | Triton X-100 | 0.1 |  | 4 | 7.1 |
|  | Cocamine oxide | 0.1 |  |  |  |
|  | carbonate buffer |  |  |  |  |
| III | peroxyacetic acid | 0.22 | 6.62 | 3 | 3.8 |
|  | acetic acid | 0.3 |  |  |  |
|  | H2O2 | ~7.0 |  | 4 | 7.1 |
|  | Triton X-100 | 0.1 |  |  |  |
|  | Cocamine oxide | 0.1 |  |  |  |
|  | carbonate buffer |  |  |  |  |

TABLE 6

Sporicidal efficacy of biocides on the base of different concentration of peroxyacetic acid against *Bacillus subtilis* spores (ATCC 19659) at different temperature

| Composition | Ingredient | Wt % of ingredient | pH | Exposure time (min) | Log reduction |
|---|---|---|---|---|---|
| I room (20° C.) | peroxyacetic acid | 0.18 | 6.09 | 3 | 0.9 |
|  | acetic acid | 0.3 |  |  |  |
|  | UREA*H2O2 | ~3.0 |  | 4 | 2.4 |

TABLE 6-continued

Sporicidal efficacy of biocides on the base of different concentration of peroxyacetic acid against *Bacillus subtilis* spores (ATCC 19659) at different temperature

| Composition | Ingredient | Wt % of ingredient | pH | Exposure time (min) | Log reduction |
|---|---|---|---|---|---|
| temperature | Triton X-100 | 0.1 | | | |
| | Cocamine oxide | 0.1 | | 5 | 5.2 |
| | carbonate buffer | | | | |
| II | peroxyacetic acid | 0.18 | | | |
| 35° C. | acetic acid | 0.3 | 6.09 | 2 | 4.7 |
| | UREA*H2O2 | ~3.0 | | | |
| | Triton X-100 | 0.1 | | 3 | 5.5 |
| | Cocamine oxide | 0.1 | | | |
| | carbonate buffer | | | 4 | 5.5 |

TABLE 7

Sporicidal efficacy of biocides on the base of peroxyacetic acid with addition of Monafax M1214 against *Bacillus subtilis* spores (ATCC 19659) at room temperature

| Composition | Ingredient | Wt % of ingredient | pH | Exposure time (min) | Log reduction |
|---|---|---|---|---|---|
| I | peroxyacetic acid | 0.15 | | 3 | 4.9 |
| | acetic acid | 0.23 | | | |
| | H2O2 | 0.75 | | | |
| | carbonate buffer I | | | | |
| II | peroxyacetic acid | 0.15 | | | |
| | acetic acid | 0.23 | | 3 | 5.6 |
| | H2O2 | 0.75 | | | |
| | Monafax M1214 | 0.1 | | | |
| | carbonate buffer I | | | | |
| III | peroxyacetic acid | 0.15 | | 3 | 5.8 |
| | acetic acid | 0.23 | | | |
| | H2O2 | 0.75 | | | |
| | Monafax M1214 | 0.38 | | | |
| | carbonate buffer I | | | | |

TABLE 8

Sporicidal efficacy of biocides on the base of peroxyacetic acid with excess of hydrogen peroxide and different additives against *Bacillus subtilis* spores (ATCC 19659) at room temperature

| Composition | Ingredient | Wt % of ingredient | pH | Exposure time (min) | Log reduction |
|---|---|---|---|---|---|
| I | peroxyacetic acid | 0.15 | | 3 | 5.4 |
| | acetic acid | 0.23 | | | |
| | H2O2 | 0.75 | | | |
| | Monafax M1214 | 0.1 | | | |
| | H-Benzotriazole | 0.1 | | | |
| | carbonate buffer I | | | | |
| II | peroxyacetic acid | 0.15 | | 3 | 6.2 |
| | acetic acid | 0.23 | | | |
| | H2O2 | ~2.8 | | | |
| | Monafax M1214 | 0.1 | | | |
| | H-Benzotriazole | 0.1 | | | |
| | carbonate buffer I | 0.01 | | | |
| III | peroxyacetic acid | 0.15 | | 3 | 6.5 |
| | acetic acid | 0.23 | | | |
| | H2O2 | ~2.8 | | | |
| | Monafax M1214 | 0.1 | | | |
| | H-Benzotriazole | 0.1 | | | |
| | Antifoam AF 86/013 | 0.01 | | | |
| | carbonate buffer I | | | | |

TABLE 9

Sporicidal efficacy of biocides on the base of peroxyacetic acid with addition of different antifoaming agents against *Bacillus subtilis* spores (ATCC 19659) at room temperature

| Composition | Ingredient | Wt % of ingredient | pH | Exposure time (min) | Log reduction |
|---|---|---|---|---|---|
| I | peroxyacetic acid | 0.2 | | | |
| | acetic acid | 0.3 | 6.44 | 4 | 5.6 |
| | H2O2 | ~3 | | | |
| | Triton X-100 | 0.1 | | | |
| | Cocamine oxide | 0.1 | | | |
| | carbonate buffer | | | | |
| II | peroxyacetic acid | 0.2 | | | |
| | acetic acid | 0.3 | 6.43 | 4 | 5.7 |
| | H2O2 | ~3.0 | | | |
| | Triton X-100 | 0.1 | | | |
| | Cocamine oxide | 0.1 | | | |
| | carbonate buffer | | | | |
| | BC Antifoam 86/013* | 0.01 | | | |
| III | peroxyacetic acid | 0.2 | 6.36 | 4 | 6.2 |
| | acetic acid | 0.3 | | | |
| | H2O2 | ~3.0 | | | |
| | Triton X-100 | 0.1 | | | |
| | Cocamine oxide | 0.1 | | | |
| | carbonate buffer | | | | |
| | BC Antifoam FG10* | 0.01 | | | |
| IV | peroxyacetic acid | 0.2 | | | |
| | acetic acid | 0.3 | 6.42 | 4 | 5.6 |
| | H2O2 | ~3.0 | | | |
| | Triton X-100 | 0.1 | | | |
| | Cocamine oxide | 0.1 | | | |
| | carbonate buffer | | | | |
| | BC Antifoam FD20PK* | 0.01 | | | |

*All Antifoaming components were from Basildon Chemical Company Limited

The claims of the invention are as follows:

1. A method of disinfecting an article comprising contacting the article with an aqueous disinfectant solution comprising from 0.10 to 0.30 wt % peroxyacetic acid; hydrogen peroxide; and a carbonate buffer in an amount sufficient to provide a pH of between 5 to 7; and wherein the weight ratio of hydrogen peroxide to peroxyacetic acid is 15:1 or greater; and wherein the carbonate buffer is provided to the aqueous disinfectant solution as at least two salts comprising i) hydrogencarbonate anions and hydroxide anions or ii) hydrogencarbonate anions and carbonate anions.

2. A method according to claim 1 wherein the carbonate buffer comprises hydrogencarbonate anions and hydroxide anions.

3. A method according to claim 2 wherein the molar ratio of hydrogencarbonate anions to hydroxide anions is about 0.9:1 to about 1.1:1.

4. A method according to claim 2 wherein the hydrogencarbonate and hydroxide anions are present in the buffer in equimolar amounts or close to equimolar amounts.

5. A method according to claim 1 wherein the carbonate buffer comprises hydrogencarbonate anions and carbonate anions.

6. A method according to claim 5 wherein the molar ratio of hydrogencarbonate anions to carbonate anions is about 0.15:1 to about 0.25:1.

7. A method according to claim 5 wherein the hydrogencarbonate and carbonate anions are present in the buffer in equimolar amounts or close to equimolar amounts.

8. A method according to claim 1 wherein the aqueous disinfectant solution further comprises a surfactant.

9. A method according to claim 8 wherein the surfactant comprises a non-ionic surfactant.

10. A method according to claim 8 wherein the surfactant is selected from the group consisting of polyoxyethylene alkyl ether phosphates, polyethylene glycol p-(1,1,3,3-tetramethylbutyl)-phenyl ether and cocoamidopropylamino oxide.

11. A method according to claim 10 wherein the weight ratio of hydrogen peroxide to peroxyacetic acid is no greater than 32:1.

12. A method according to claim 11 wherein the at least two salts of the carbonate buffer further comprise cations of sodium and/or potassium.

13. A method according to claim 8 wherein the surfactant comprises a polyoxyethylene alkyl ether phosphate.

14. A method according to claim 1 wherein the aqueous disinfectant solution further comprises a corrosion inhibitor.

15. A method according to claim 14 wherein the corrosion inhibitor comprises a benzotriazole.

16. A method according to claim 1 wherein the at least two salts of the carbonate buffer further comprise cations of sodium and/or potassium.

17. A method according to claim 1 wherein the weight ratio of hydrogen peroxide to peroxyacetic acid is no greater than 32:1.

18. A method according to claim 1 wherein the weight ratio of hydrogen peroxide to peroxyacetic acid is 30:1 or greater.

19. A method according to claim 1 wherein the aqueous disinfectant solution further comprises an antifoaming agent.

20. A method according to claim 1 wherein disinfection is carried out in a temperature range of 15–40° C.

21. A method according to claim 1 wherein disinfection is carried out in a temperature range of 20–35° C.

22. A method according to claim 1 wherein disinfection is carried out at ambient temperature.

* * * * *